United States Patent [19]

Dales et al.

[11] Patent Number: 4,501,696
[45] Date of Patent: Feb. 26, 1985

[54] PROCESS FOR THE PREPARATION OF PENAM DERIVATIVES

[75] Inventors: John R. M. Dales, Littlehampton; Marguerita A. Vallance, Worthing, both of England

[73] Assignee: Beecham Group p.l.c., England

[21] Appl. No.: 396,646

[22] Filed: Jul. 9, 1982

[30] Foreign Application Priority Data

Jul. 10, 1981 [GB] United Kingdom ............... 8121303

[51] Int. Cl.³ .................. C07D 499/04; A61K 31/425
[52] U.S. Cl. .................. 260/245.2 R; 260/239.1; 260/245.2 T
[58] Field of Search ............ 544/21; 260/245.2 R, 260/239.1; 424/246

[56] References Cited

U.S. PATENT DOCUMENTS

| | | | |
|---|---|---|---|
| 3,897,424 | 7/1975 | Kippel et al. | 544/21 |
| 3,910,902 | 10/1975 | Dolfini et al. | 544/21 |
| 3,954,731 | 5/1976 | Spitzer et al. | 544/21 |
| 4,048,320 | 9/1977 | Clayton et al. | 424/271 |
| 4,062,842 | 12/1977 | Dolfini et al. | 260/239.1 |
| 4,260,625 | 4/1981 | Hardy et al. | 424/271 |
| 4,308,259 | 12/1981 | Bentley | 424/200 |

FOREIGN PATENT DOCUMENTS

| | | |
|---|---|---|
| 27010 | 4/1981 | European Pat. Off. . |
| 1339007 | 11/1973 | United Kingdom . |
| 1439898 | 6/1976 | United Kingdom . |
| 1538051 | 1/1979 | United Kingdom . |

*Primary Examiner*—Nicholas S. Rizzo
*Attorney, Agent, or Firm*—Jacobs & Jacobs

[57] ABSTRACT

A process for the preparation of a penam derivative of formula (I):

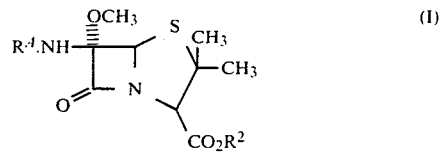

wherein $R^A$ is hydrogen or a group of formula (Ia):

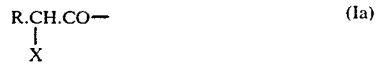

wherein X is $-CO_2R^1$, or $SO_3R^1$; R is $C_{1-6}$alkyl, aryl, or heterocyclyl; $R^1$ is hydrogen, or a pharmaceutically acceptable salt-forming ion or ester-forming radical, and $R^2$ represents hydrogen or a pharmaceutically acceptable salt-forming ion or in vivo hydrolyzable ester-forming radical; which process comprises reacting a compound of formula (II):

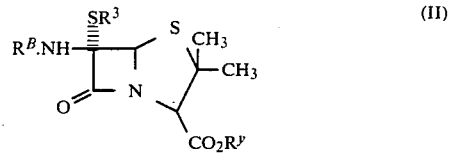

wherein $R^B$ is hydrogen, a removable amino blocking group, or a group of formula (IIa):

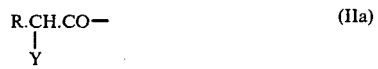

wherein Y is $-CO_2R^x$ or $-SO_3R^x$; R is as defined with respect to formula (I) above; $R^x$ represents an ester-forming radical, $R^y$ represents hydrogen, a salt-forming radical or a carboxyl-blocking group, and $R^3$ represents an alkyl, benzyl, or aryl group; with methanol in the presence of copper ions; and thereafter if necessary carrying out one or more of the following steps:

(i) removal of any blocking group;
(ii) converting the product to a pharmaceutically acceptable salt or ester thereof.

11 Claims, No Drawings

PROCESS FOR THE PREPARATION OF PENAM DERIVATIVES

This invention relates to a process for the preparation of antibacterially active penam derivatives having a 6α-methoxy substituent.

The present invention provides a process for the preparation of a penam derivative of formula (I):

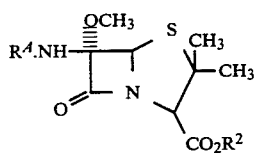

wherein $R^A$ is hydrogen or a group of formula (Ia):

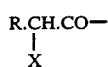

wherein X is $-CO_2R^1$, or $SO_3R^1$; R is $C_{1-6}$alkyl, aryl, or heterocyclyl; $R^1$ is hydrogen, or a pharmaceutically acceptable salt-forming ion or ester-forming radical, and $R^2$ represents hydrogen or a pharmaceutically acceptable salt-forming ion or in vivo hydrolysable ester-forming radical; which process comprises reacting a compound of formula (II):

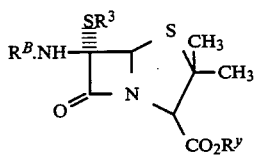

wherein $R^B$ is hydrogen, a removable amino blocking group, or a group of formula (IIa):

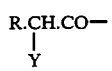

wherein Y is $-CO_2R^x$ or $-SO_3R^x$; R is as defined with respect to formula (I) above; $R^x$ represents an ester-forming radical, $R^y$ represents hydrogen, a salt-forming radical or a carboxyl-blocking group, and $R^3$ represents an alkyl, benzyl, or aryl group; with methanol in the presence of copper ions; and thereafter if necessary carrying out one or more of the following steps:
 (i) removal of any blocking group;
 (ii) converting the product to a pharmaceutically acceptable salt or ester thereof.

Suitable examples of the group R include $C_{1-6}$alkyl; an optionally substituted 5-membered heterocyclic ring containing one or two heteroatoms selected from oxygen, sulphur and nitrogen; phenyl; mono-substituted phenyl where the substituent is halogen, hydroxy, $C_{1-6}$alkoxy, nitro, amino, $C_{1-6}$alkyl, $C_{1-6}$haloalkyl, $C_{1-6}$alkylcarbonyloxy, or $C_{1-6}$alkyl sulphonylamino (for example $-NHSO_2CH_3$); or di-substituted phenyl where the substituents are selected from hydroxy, halogen, methoxy, acetoxy and amino.

Suitably R is phenyl; mono-substituted phenyl where the substituent is fluorine, chlorine, hydroxy, methoxy, nitro, amino, acetoxy or trifluoromethyl; or di-substituted phenyl where the substituents are selected from acetoxy, hydroxy, and methoxy.

Suitable $C_{1-6}$alkyl groups for the groups R and $R^1$ include methyl, ethyl, n- and iso-propyl, n-, iso-, sec- and tert-butyl.

Suitable 5-membered heterocyclic rings for the group R include furyl, thienyl, oxazolyl, thiazolyl, isoxazolyl, iso-thiazolyl, imidazolyl; each such group may be substituted by various groups for example halogen, hydroxy, amino, or $C_{1-6}$alkyl. Particular examples of such groups include 2- or 3-thienyl and 2-aminothiazolyl.

Specific examples of the group R include phenyl, 2- or 3-thienyl, p-hydroxyphenyl, p-aminophenyl and p-acetoxyphenyl.

A preferred example of the group $R^B$ is hydrogen.

Suitable pharmaceutically acceptable salt-forming ions for the groups $R_1$ and $R^2$ include metal salts, e.g aluminium, alkali metal salts such as sodium or potassium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabeitylamine, N,N'-bisdehydroabietylethylenediamine, or bases of the pyridine type such as pyridine, collidine or quinoline, or other amines which have been used to form salts with known penicillins.

The salt-forming ions included within the definition of the group $R^y$ include the above mentioned ions and also include other salt-forming ions which are not necessarily pharmaceutically acceptable.

When the group $R^2$ represents a pharmaceutically acceptable in vivo hydrolysable ester-forming radical, such esters are those which hydrolyse readily in the human body to produce the parent acid, and include, for example, acyloxyalkyl groups such as acetoxymethyl, pivaloyloxymethyl, α-acetoxyethyl, α-acetoxybenzyl and α-pivaloyloxyethyl groups; alkoxycarbonyloxyalkyl groups, such as ethoxycarbonyloxymethyl and α-ethoxycarbonyloxyethyl; dialkylaminoalkyl groups such as dimethylaminomethyl, dimethylaminoethyl, diethylaminomethyl or diethylaminoethyl; and lactone groups such as phthalidyl or dimethoxyphthalidyl.

The group $R^1$ may be any of the ester-forming radicals as specified for the group $R^2$ and in addition $R^1$ may represent other pharmaceutically acceptable ester-forming groups such as alkyl, aryl or aralkyl groups any of which may be substituted. Examples of such groups include:
 (a) $C_{1-6}$alkyl such as methyl, ethyl, n- and iso-propyl, n-, sec-, iso- and tert-butyl;
 (b) substituted $C_{1-6}$alkyl wherein the substituent is at least one of: chloro, bromo, fluoro, nitro, $C_{1-6}$alkoxy, $C_{1-6}$alkoxycarbonyl, cyano, $C_{1-6}$alkylthio, $C_{1-6}$alkylamino;
 (c) phenyl, benzyl or substituted phenyl or benzyl wherein the substituent is at least one of chloro, bromo, fluoro, $C_{1-6}$alkyl, $C_{1-6}$alkoxy, $C_{1-6}$alkanoyl, $C_{1-6}$alkoxycarbonyl, nitro or di-($C_{1-6}$)alkylamino.

Preferred ester-forming radicals $R^1$ include $C_{1-6}$alkyl, benzyl, phthalidyl, indanyl, phenyl and mono-, di and tri-($C_{1-6}$)-alkyl substituted phenyl such as o-, m-, or p-methylphenyl, ethylphenyl, n- or iso-propylphenyl, or n-, sec-, iso- or t-butylphenyl.

Suitable carboxyl-blocking groups for the group $R^y$ are those which may be readily removed from the carboxylic acid under conventional conditions at a later stage of the reaction. Such groups include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, an oxime radical of formula $-N=CHR^o$ where $R^o$ is aryl or heterocyclic, or an in vivo hydrolysable ester radical such as defined above.

The carboxyl group may be regenerated from any of the above esters by usual methods appropriate to the particular $R^y$ group, for example, acid- and base-catalysed hydrolysis, or by enzymically-catalysed hydrolysis, or by hydrogenation.

When it is desired to produce a compound of formula (I) wherein the group $R^1$ is hydrogen or a salt-forming ion, by the process of this invention, a compound of formula (II) is employed wherein $R^x$ is a blocking group. For the preparation of a compound of formula (I) wherein $R^1$ is a pharmaceutically acceptable ester-forming radical, a compound of formula (II) is employed wherein $R^x$ represents the desired $R^1$ group.

When the group R represents p-hydroxyphenyl, it may if desired be protected by means of a group which is readily removed chemically after the process of the invention. Such protecting groups include trialkylsilyl groups.

Suitable examples of the alkyl group $R^3$ include $C_{1-6}$alkyl groups such as methyl, ethyl, n- or iso-propyl, and n-, sec-, iso, or tert-butyl groups.

A preferred alkyl group for $R^3$ is methyl.

Suitable examples of the aryl group $R^3$ include phenyl, optionally substituted with $C_{1-6}$alkyl, $C_{1-6}$alkoxy, halogen, or nitro. Preferred aryl groups for $R^3$ include phenyl, o-, m- or p-methylphenyl, o-, m- or p-nitrophenyl, in particular p-methylphenyl.

A suitable temperature range for the process of this invention is from 0° C. to 40° C., conveniently 20° C. to 30° C., preferably about 25° C. The time required for the reaction depends on the temperature and the reagents employed. Generally, the reaction is complete within one hour. The methanol used in the process is conveniently employed as a solvent for the reaction mixtures. Other compatible co-solvents may be additionally used if desired, for example, ethyl acetate, methyl isobutyl ketone and preferably isopropyl acetate. It will be appreciated that to give reasonable rate and extent of reaction that the reagents and starting materials should have at least partial solubility in the solvent system employed.

Suitable sources of copper ion include sources of cuprous or cupric ion. Suitable sources of copper ion include for example cuprous or cupric salts of carboxylic acid such as for example, cupric acetate, cuprous acetate, cupric formate, cupric propionate or cupric chloride, cupric sulphate or cupric nitrate.

When the group $R^B$ represents hydrogen, it is advantageous to carry out the reaction in the presence of organic base. Suitable organic bases include triethylamine, and preferably pyridine.

The starting material for the process of this invention, ie compound of formula (II) above, where $R^B$ is not hydrogen, is disclosed, although not claimed, in U.S. Pat. No. 3,965,093. It may be prepared by acylation, under conventional conditions of the compound (II) where $R^B$ is hydrogen, ie a 6-amino compound of formula (III) or a salt or ester thereof:

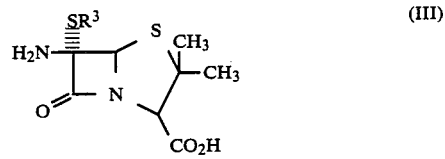

wherein $R^3$ is as defined with respect to formula (II) above. Compounds of formula (III) may be prepared from a Schiff's base derivative as described in U.S. Pat. No. 3,965,093, or may be prepared by reacting a thiooxime compound of formula (IV):

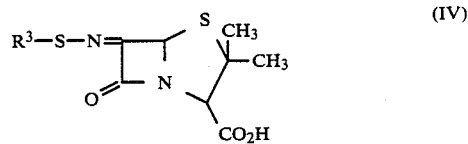

(where $R^3$ is as defined with respect to formula (II) above) with a tri(alkyl)phosphine or tri(aryl)phosphine, followed by treatment with an acid catalyst such as silica gel. That process is described in U.S. Pat. No. 4,119,778 and in J Amer Chem Soc, 1977, 99, 5504.

The compounds of formula (I) wherein $R^4$ is not hydrogen, which are prepared by the process of this invention have good antibacterial activity, as disclosed in British Pat. Nos. 1,538,051 and 1,538,052. The compounds of formula (I) wherein $R^4$ is hydrogen are useful as chemical intermediates.

The following Examples illustrate the process of this invention.

EXAMPLE 1

Preparation of benzyl 6β-amino-6α-methoxypenicillanate from benzyl 6β-amino-6α-methylthiopenicillanate Benzyl 6β-amino-6α-methylthiopenicillanate (17.6 g, 0.05 mole), methanol (140 ml) and pyridine (10 ml) were dissolved in isopropyl acetate (300 ml) and the solution warmed to 25° C. Cupric acetate monohydrate (11.03 g, 0.055 mole) was added and the solution stirred and maintained at 25° C. for 40 minutes. The reaction mixture was cooled to 0° C., celite was added and the resulting slurry was filtered through a celite pad. The celite cake was washed with isopropyl acetate (2×50 ml) and the wash solution was combined with the filtrate. The bulked organic phases were washed with two water/saturated brine mixtures (300 ml/100 ml) and (100 ml/100 ml). The solution was then washed with a 1% solution of sodium sulphide (200 ml) and the black emulsion which formed was filtered through a celite pad. The celite cake was washed with an isopropyl acetate/water mixture (150 ml/150 ml) and the wash solution combined with the filtrate. Brine (300 ml) was added to the filtrate to improve separation and the organic layer was removed and washed with 0.1% sodium sulphide solution (2×100 ml), water (2×100 ml) and a brine/water mixture (50 ml/50 ml). The isopropyl acetate solution was dried over magnesium sulphate. The solution was filtered and the magnesium sulphate cake was washed with isopropyl acetate (2×50 ml). The wash solution was combined with the filtrate and the resulting solution evaporated to an orange oil (water bath temperature 35° C.).

The weight yield was 20.1 g of 77.4% purity 6-methoxy-penicillin having an activity yield of 92.6%.

EXAMPLE 2

Preparation of benzyl 6β-amino-6α-methoxypenicillanate from benzyl 6β-amino-6α-methylthiopenicillanate toluene-4-sulphonic acid salt Benzyl 6β-amino-6α-methylthiopenicillanate toluene-4-sulphonic acid salt (26.25 g 0.05 mole) was stirred with isopropyl acetate (150 ml) and saturated sodium bicarbonate solution (100 ml) until all the solid had dissolved. The organic phase was separated and the aqueous phase extracted with isopropyl acetate (2×50). The organic phases were combined and washed with water (50 ml) and brine (50 ml) and then dried over magnesium sulphate. The solution was filtered and the magnesium sulphate cake was washed with isopropyl acetate (50 ml).

The resulting isopropyl acetate solution containing the benzyl 6β-amino-6α-methylthiopenicillanate was reacted according to the conditions given in Example 1.

The weight yield was 21.7 g of 68.5% purity 6-methoxy-penicillin having an activity yield of 88.5%.

EXAMPLE 3

Preparation of benzyl 6β-amino-6α-methoxypenicillanate from benzyl 6β-amino-6α-(4-methylphenylthio)penicillanate benzene sulphonic acid salt Benzyl 6β-amino-6α-(4-methylphenylthio)penicillanate benzene sulphonic acid (29.3 g 0.05 mole) was subjected to the neutralisation and extraction procedure described in Example 2.

The resulting isopropyl acetate solution was reacted according to the conditions given in Example 1 except that the reaction time at 25° C. was extended to 80 minutes.

The weight yield was 19.2 g of 70.8% purity 6-methoxypenicillin having an activity yield of 80.9%.

EXAMPLE 4

Preparation of benzyl 6β-amino-6α-methoxypenicillanate from benzyl 6β-amino-6α-methylthiopenicillanate and cupric acetate The reaction was carried out as Example 1 except that ethyl acetate was used instead of isopropyl acetate as the reaction solvent.

The weight yield was 20.7 g of 73.9% purity 6-methoxy-penicillin having an activity yield of 91.0%.

EXAMPLE 5

Preparation of benzyl 6β-amino-6α-methoxypenicillanate from benzyl 6β-amino-6α-methylthiopenicillanate and cupric acetate in methanol as the only reaction solvent Benzyl 6β-amino-6α-methylthiopenicillanate (17.6 g, 0.05 mole) was dissolved in a mixture of methanol (440 ml) and pyridine (10 ml). The solution was warmed and stirred at 25° C. and treated with cupric acetate monohydrate (11.03 g, 0.055 mole). The solution was stirred and maintained at 25° C. for 5 minutes. The reaction mixture was evaporated to an oil (water bath temperature 35° C.). The oil was slurried in isopropyl acetate (300 ml) for 10 minutes. The slurry was cooled to 0° C., celite was added and the resulting slurry was filtered through a celite pad. The celite cake was washed with isopropyl acetate (2×50 ml) and the washed solution was combined with the filtrate. The bulked organic phases were washed with two water/saturated brine mixtures (300 ml/100 ml) and (100 ml/100 ml), water (2×100 ml) and a brine/water mixture (50 ml/50 ml). The isopropyl acetate solution was dried over magnesium sulphate. The solution was filtered and the magnesium sulphate cake was washed with isopropyl acetate (2×50 ml). The washed solution was combined with the filtrate and the resulting solution evaporated to an orange oil. (Water bath temperature 35° C.).

The weight yield was 21.6 g of 60.9% purity 6-methoxypenicillin having an activity yield of 78.3%.

EXAMPLE 6

Preparation of benzyl 6β-amino-6α-methoxypenicillanate from benzyl 6β-amino-6α-methylthiopenicillanate and cuprous acetate The isopropyl acetate solution of benzyl 6β-amino-6α-methylthiopenicillanate was reacted according to the conditions in Example 1 except that cuprous acetate (95%, 7.1 g, 0.05 mole) was used instead of cupric acetate monohydrate, and the reaction time at 25° C. was reduced to 15 minutes.

The weight yield was 20.9 g of 71.1% purity 6-methoxypenicillin having an activity yield of 88.5%

EXAMPLE 7

Preparation of benzyl 6β-amino-6α-methoxypenicillanate from benzyl 6β-amino-6α-methylthiopenicillanate and cupric formate The isopropyl acetate solution of benzyl 6β-amino-6α-methylthiopenicillanate was reacted according to the conditions in Example 1 except that cupric formate tetrahydrate (12.4 g, 0.055 mole) was used instead of cupric acetate monohydrate and the reaction time at 25° C. was reduced to 30 minutes.

The weight yield was 19.8 g of 74.2% purity 6-methoxypenicillin having an activity yield of 87.5%.

EXAMPLE 8

Preparation of benzyl 6β-amino-6α-methoxypenicillanate from benzyl 6β-amino-6α-methylthiopenicillanate and cupric sulphate The isopropyl acetate solution of benzyl 6β-amino-6α-methylthiopenicillanate was reacted according to the conditions in Example 1 except that cupric sulphate pentahydrate (13.73 g, 0.055 mole) was used instead of cupric acetate monohydrate and the reaction time at 25° C. was extended to 50 minutes. The product was isolated as a brown oil.

The weight yield was 16.9 g, of 14.6% purity 6-methoxypenicillin having an activity yield of 14.7%.

EXAMPLE 9

Preparation of benzyl 6β-amino-6α-methoxypenicillanate from benzyl 6β-amino-6α-methylthiopenicillanate and cupric nitrate The isopropyl acetate solution of benzyl 6β-amino-6α-methylthiopenicillanate was reacted according to the conditions in Example 1 except that cupric nitrate trihydrate (13.29 g, 0.055 mole) was used instead of cupric acetate monohydrate and the reaction time of 25° C. was reduced to 5 minutes. The product was isolated as a brown oil.

The weight yield was 17.3 g of 20.9% purity 6-methoxypenicillin having an activity yield of 21.5%.

EXAMPLE 10

Preparation of benzyl 6β-amino-6α-methoxypenicillanate from benzyl 6β-amino-6α-methylthiopenicillanate and cupric chloride The isopropyl acetate solution of benzyl 6β-amino-6α-methylthiopenicillanate was reacted according to the conditions in Example 1 except that cupric chloride (7.39 g, 0.055 mole) was used instead of cupric acetate monohydrate, and the reaction time at 25° C. was extended to 4 hours. The product was isolated as a brownish sticky solid.

The weight yield was 16.8 g of 6.3% purity 6-methoxypenicillin having an activity yield of 6.3%.

EXAMPLE 11

Preparation of benzyl 6β-amino-6α-methoxypenicillanate from benzyl 6β-amino-6α-methylthiopenicillanate and cupric propionate The isopropyl acetate solution of benzyl 6β-amino-6α-methylthiopenicillanate was reacted according to the conditions in Example 1, except that cupric propionate (11.5 g, 0.055 mole) was used instead of cupric acetate monohydrate and the reaction time at 25° C. was reduced to 30 minutes.

The weight yield was 19.2 g of 65.0% purity 6-methoxypenicillin having an activity yield of 74.5%.

EXAMPLE 12

Preparation of benzyl 6β-amino-6α-methoxypenicillanate from benzyl 6β-amino-6α-methylthiopenicillanate and cupric acetate without pyridine present The isopropyl acetate solution of benzyl 6β-amino-6α-methylthiopenicillanate was reacted according to the conditions in Example 1, except that pyridine was omitted from the reaction.

The weight yield was 20.8 g of 76.5% purity methoxy pencillin having an activity yield of 76.5%.

We claim:

1. A process for the preparation of a penam derivative of formula (I):

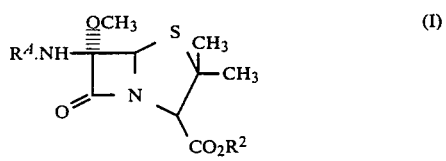

wherein $R^A$ is hydrogen or a group of formula (Ia):

wherein X is $-CO_2R^1$, or $SO_3R^1$; R is $C_{1-6}$alkyl, an optionally substituted 5-membered heterocylic ring containing one or two heteroatoms selected from oxygen, sulphur and nitrogen; phenyl; mono-substituted phenyl where the substituent is halogen, hydroxy, $C_{1-6}$alkoxy, nitro, amino, $C_{1-6}$alkyl, $C_{1-6}$haloalkyl, $C_{1-6}$alkylcarbonyloxy, or $C_{1-6}$alkylsulphonylamino; or di-substituted phenyl where the substituents are selected from hydroxy, halogen, methoxy, acetoxy, and amino; $R^1$ is hydrogen, or a pharmaceutically acceptable salt-forming ion or ester-forming radical, and $R^2$ represents hydrogen or a pharmaceutically acceptable salt-forming ion or in vivo hydrolysable ester-forming radical; which process comprises reacting a compound of formula (II):

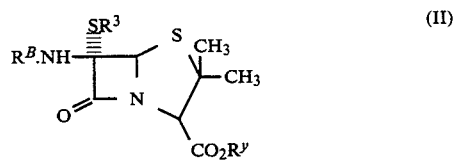

wherein $R^B$ is hydrogen, a removable amino blocking group, or a group of formula (IIa):

wherein Y is $-CO_2R^x$ or $-SO_3R^x$; R is as defined with respect to formula (Ia) above; $R^x$ represents an ester-forming radical, $R^Y$ represents hydrogen, a salt-forming radical or a carboxyl-blocking group, and $R^3$ represents an alkyl, benzyl, or aryl group; with methanol in the presence of copper ions; and thereafter if necessary carrying out one or more of the following steps:
  (i) removal of any blocking group;
  (ii) converting the product to a pharmaceutically acceptable salt or ester thereof.

2. A process as claimed in claim 1 wherein R is phenyl; mono-substituted phenyl where the substituent is fluorine, chlorine, hydroxy, methoxy, nitro, amino, acetoxy or trifluoromethyl; or di-substituted phenyl where the substituents are selected from acetoxy, hydroxy, and methoxy.

3. A process as claimed in claim 1 wherein $R^B$ is hydrogen.

4. A process as claimed in claim 1 wherein $R^3$ is $C_{1-6}$alkyl.

5. A process as claimed in claim 1 wherein $R^3$ is methyl.

6. A process as claimed in claim 1 wherein $R^3$ is phenyl, optionally substituted with $C_{1-6}$alkyl, $C_{1-6}$alkoxy, halogen or nitro.

7. A process as claimed in claim 6 wherein $R^3$ is p-methylphenyl.

8. A process as claimed in claim 1 wherein the source of copper ion is a cuprous or cupric salt of a carboxylic acid.

9. A process as claimed in claim 1 wherein the source of copper ion is cuprous or cupric acetate.

10. A process for the preparation of benzyl 6β-amino-6α-methoxypenicillanate which comprises reacting 6β-amino-6α-methylthiopenicillanate with methanol in the presence of copper ions.

11. A process according to claim 10 wherein the 6β-amino-6α-methylthiopenicillanate is in the form of its toluene-4-sulphonic acid salt.

* * * * *